(12) United States Patent
Alic et al.

(10) Patent No.: US 9,423,338 B2
(45) Date of Patent: Aug. 23, 2016

(54) APPARATUS AND APPARATUS CONTROL METHOD FOR THE QUANTITATIVE CONCENTRATION DETERMINATION OF SELECTED SUBSTANCES FILTERED OUT OF A PATIENT'S BODY IN A FLUID

(71) Applicant: B. BRAUN AVITUM AG, Melsungen (DE)

(72) Inventors: Miran Alic, Melsungen (DE); Christof Strohhoefer, Kassel (DE); Waldemar Janik, Hessisch Lichtenau (DE)

(73) Assignee: B. BRAUN AVITUM AG, Melsungen (DE)

( * ) Notice: Subject to any disclaimer, the term of this patent is extended or adjusted under 35 U.S.C. 154(b) by 0 days.

(21) Appl. No.: 14/691,208

(22) Filed: Apr. 20, 2015

(65) Prior Publication Data

US 2015/0323447 A1 Nov. 12, 2015

(30) Foreign Application Priority Data

May 8, 2014 (DE) .......................... 10 2014 106 489

(51) Int. Cl.
*G01N 21/00* (2006.01)
*G01N 21/25* (2006.01)
(Continued)

(52) U.S. Cl.
CPC .......... *G01N 21/255* (2013.01); *A61M 1/1617* (2014.02); *G01N 21/3103* (2013.01);
(Continued)

(58) Field of Classification Search
CPC ................... G01N 35/10; G01N 2035/00326; G01N 2035/00495; G01N 35/026; G01N 2035/00425; G01N 21/25; G01N 35/00871; G01N 35/1065; G01N 15/1475; G01N 2015/008; G01N 2015/1486; G01N 2035/00356
See application file for complete search history.

(56) References Cited

U.S. PATENT DOCUMENTS

| | | | |
|---|---|---|---|
| 4,229,542 A | 10/1980 | Nylen et al. | |
| 5,387,524 A * | 2/1995 | Hayashibe | G01N 33/84 436/164 |

(Continued)

FOREIGN PATENT DOCUMENTS

| | | |
|---|---|---|
| DE | 26 58 101 | 7/1977 |
| DE | 10 2011 101 193 | 11/2012 |

(Continued)

OTHER PUBLICATIONS

German Search Report for DE 10 2014 106 489.5 dated Jul. 28, 2014.

(Continued)

*Primary Examiner* — Michael P Stafira
(74) *Attorney, Agent, or Firm* — RatnerPrestia (57) ABSTRACT

Methods and apparatus are disclosed for determining a substance in a fluid excreted/extracted from the body or spent dialysate, e.g., for determining a quality measure for the dialysis, such as the concentration of selected toxic substances, and/or for determining a removed total quantity of uremic toxins during a dialysis with a dialysis apparatus. A concentration of a substance in the fluid may be determined by: detecting, by an absorption sensor, a first extinction signal of the fluid at an analysis wavelength at a defined first pH value of the fluid; adjusting, by a pH adjusting device, a second pH value of the fluid which differs from the first pH value; detecting, by the absorption sensor, a second extinction signal of the fluid at the analysis wavelength at the second pH value; and processing/comparing the two extinction signals for the first and the second pH values and determining an absolute concentration of the substance dissolved in the fluid.

16 Claims, 4 Drawing Sheets

(51) Int. Cl.
*G01N 21/31* (2006.01)
*A61M 1/16* (2006.01)
*G01N 21/85* (2006.01)
*G01N 21/33* (2006.01)

(52) U.S. Cl.
CPC ....... *A61M2205/3313* (2013.01); *G01N 21/33* (2013.01); *G01N 21/85* (2013.01); *G01N 2201/061* (2013.01); *G01N 2800/347* (2013.01)

(56) References Cited

U.S. PATENT DOCUMENTS

| | | | |
|---|---|---|---|
| 5,928,180 | A | 7/1999 | Krivitski et al. |
| 7,002,670 | B2 | 2/2006 | Wariar et al. |
| 2008/0015434 | A1 | 1/2008 | Rubinstein et al. |
| 2008/0285011 | A1* | 11/2008 | Shakespeare .......... G01N 21/33 356/51 |
| 2008/0285012 | A1* | 11/2008 | Shakespeare .......... G01N 21/33 356/51 |
| 2011/0224516 | A1* | 9/2011 | Romey .............. A61B 5/14532 600/317 |

FOREIGN PATENT DOCUMENTS

| | | |
|---|---|---|
| DE | 10 2011 102 962 | 11/2012 |
| EP | 0 911 043 | 4/1999 |
| EP | 1 083 948 | 3/2001 |
| GB | 2 390 420 | 1/2004 |
| WO | WO 96/18096 | 6/1996 |
| WO | WO 99/62574 | 12/1999 |
| WO | WO 2009/071102 | 6/2009 |
| WO | WO 2010/024963 | 3/2010 |
| WO | WO 2011/147425 | 12/2011 |
| WO | WO 2012/152514 | 11/2012 |
| WO | WO 2014/026828 | 2/2014 |

OTHER PUBLICATIONS

Tomson, et al., "Optical measurement of creatinine in spent dialysate," Clinical Technology, vol. 79, No. Feb. 2013 (107-117).

EP Search Report (with translation) for EP 15157737 dated Sep. 18, 2015.

* cited by examiner

APPARATUS AND APPARATUS CONTROL METHOD FOR THE QUANTITATIVE CONCENTRATION DETERMINATION OF SELECTED SUBSTANCES FILTERED OUT OF A PATIENT'S BODY IN A FLUID

CROSS REFERENCE TO RELATED APPLICATIONS

This application claims priority to German application DE 10 2014 106 489.5 filed May 8, 2014, the contents of such application being incorporated by reference herein.

FIELD OF THE INVENTION

The present invention relates to an apparatus and to an apparatus control method for the quantitative concentration determination of selected or selectable substances filtered out (naturally or synthetically) of a patient's body, preferably selected uremic toxins in an extracorporeal blood purification fluid, in particular a dialysis apparatus for the synthetic removal of uremic toxins from a patient's blood circulation, and an apparatus control method for determining a quality measure for the dialysis, preferably the concentration of selected toxic substances, and/or for the determination of a removed total quantity of uremic toxins during a dialysis (determination of a clearance during a dialysis), preferably related to selected/selectable toxic substances removed from a patient's blood, preferably creatinine and/or uric acid.

BACKGROUND OF THE INVENTION

Uremic toxins are all substances which have to be excreted renally. These uremic toxins accumulate in the body of a human being/patient having lacking/reduced renal function. The kidney substitution therapy, for instance, in the form of a hemodialysis (HD) therapy, offers the possibility of treating the patient in that uremic toxins from the intracorporeal circulation of the patient are transferred to a circulation with dialysis fluid with a dialyzer. In this process, the patient's blood is guided via an extracorporeal blood circulation into the dialyzer at the blood side thereof and is subsequently resupplied into the patient's intracorporeal blood circulation. At the other dialysate side the dialyzer is supplied through an inlet for dialysate with fresh dialysate which absorbs the uremic toxins. The spent dialysate finally leaves the dialyzer through an outlet for dialysate.

The dialysate is in general an aqueous bicarbonate buffer solution having properties similar to those of blood with respect to the pH value and the electrolyte composition. In the course of a hemodialysis therapy the dialysate gets into contact with a patient's blood via a membrane within the dialyzer. Uremic toxins in the range of 18-65k daltons may thus diffuse in the dialyzer from the patient's blood into the dialysate, so that fresh dialysate at the inlet becomes the spent dialysate at the outlet.

The quality of a blood purification therapy such as a dialysis therapy may be assessed in that the quantity of uremic toxins in the dialysate is detected before and after the treatment. It is, however, not only important to obtain knowledge about the loading of the spent dialysate with uremic toxins as such, but the knowledge about the composition of the uremic toxins may also be of interest. With some uremic toxins such as creatinine it is namely possible to make statements, for instance, with respect to a patient's nutritional status. Therefore, both the absolute quantity of extracted uremic toxins and their composition are of significance.

Some uremic toxins absorb light in the range between 190 nm and 350 nm. The absorption may be utilized to determine the concentration of uremic toxins in the dialysate at the outlet side. The absorption of light may be measured with optical sensors, e.g. with optical absorption sensors such as they are sufficiently known from the state of the art. Optical absorption sensors are devices determining the absorption of a substance or of a substance mixture on the basis of a transmission measurement. With the aid of the Bouguer-Lambert-Beer law at one or a plurality of optical wavelengths it is also possible to determine the concentration of absorbing compounds (e.g. creatinine, uric acid, etc.), for instance, in optically clear fluids. Although the absorption sensor physically measures a transmission, the signal is often output as a decadic absorption measure. The decadic absorption measure is proportional to the molar extinction coefficient, the concentration and the optical path length. In general, the path length is predetermined by the sensor geometry and is thus a constant. The same applies to the molar extinction coefficient which is a specific substance property. For a given wavelength it is constant. In the end, the decadic absorption measure in a sensor is directly proportional to the only remaining variable factor, namely the concentration of a marker. This, however, applies only to solutions with one single dissolved substance.

The difficulty arising during the examination of solutions with a plurality of components is, however, the distinct allocation of an absorption signal to the concentration of a component. This is particularly the case if the absorption bands of the interesting substances overlap each other (such as, for instance, creatinine and uric acid) or with uninteresting substances.

When it comes to the therapy-accompanying determination of a measure for dialysis quality, the qualitative measure Kt/V is presently used, with K clearance (is determined e.g. by the urea content of the blood before and after the dialysis—the clearance results in particular from a comparison of the concentration of urea at the blood inlet with the concentration of urea at the blood outlet of the dialyzer)

t effective dialysis time in minutes, and

V the part of the body volume in which urea is distributed

Since this measure is qualitative, it does not allow any statements about the actually removed quantities of a particular substance such as e.g. creatinine. The market, however, demands also a quantitative measure of a selected substance which renders it possible to make further statements about the patient. Thus, the duration of the dialysis may still be controlled without problems via the removed total quantity of a marker, but additionally a trend about several therapies may be made which allows assessing the nutritive state of the respective patient, for instance, in the case of creatinine.

Basically there exist methods under laboratory conditions, in particular enzymatic tests, which are capable of determining creatinine concentrations in serum. However, e.g. one or two measurements of the creatinine concentration in the blood are not sufficient for determining the removed quantity of creatinine in quantitative respect. This is substantially due to the fact that the removal function, i.e. the function indicating the concentration in the blood or in the dialysate during a dialysis, is unknown.

Therefore, a higher-frequent measurement of the creatinine concentration in the blood or in the spent dialysate is required. The measurement in the spent dialysate has turned out to be advantageous as compared to the measurement in the blood. The spent dialysate always contains the actually removed quantity of creatinine as compared to blood in which various processes cause the rediffusing of creatinine and thus distort the determination of the actually removed quantity.

DESCRIPTION OF THE RELATED ART

From "Real-time Kt/V determination by ultraviolet absorbance in spent dialysate: technique validation", Kidney International advance online publication, 14-Jul. 2010; doi: 10.1038/ki.2010.216, and from "Dialysis dose (Kt/V) and clearance variation sensitivity using measurement of ultraviolet-absorbance (on-line), blood urea, dialysate urea and ionic dialysance", Nephrol Dial Transplant (2006) 21: 2225-2231 doi:10.1093/ndt/gfl147, Advance Access publication 12 Apr. 2006, concepts based on UV measurements are known by which the dimensionless relation Kt/V for urea is measured. K is the clearance in ml/min, V the volume to be purified (urea distribution volume) in ml, and t the dialysis duration in min. In the concepts described there, an absorption signal in the wavelength range of 280 nm to 350 nm is correlated with the removal rate of urea. By linking an absorption signal with the urea concentration this device is capable of making corresponding statements about the value of Kt/V by measuring an absorption value at a particular wavelength.

A disadvantage of this concept consists in that a quantitative indication of the total quantity of the removed urea is not possible. Moreover, a statement about the composition of the uremic toxins examined cannot be made. By the relative indication of a value for Kt/V the quality of a dialysis is described insufficiently only.

From "Optical measurement of creatinine in spent dialysate", Ruth Tomson, Ivo Fridolin, Frederik Uhlin, Jana Holmar, Kai Lauri and Merike Luman, a method for determining the creatinine concentrations in spent dialysate is known. The method is based on the assumption that extinction values of spent dialysate at different wavelengths may be used to obtain a prediction model for the determination of the creatinine concentration.

With the method according to this state of the art it is, however, not possible to ensure the required exactness (for instance, of approx. +/−10%).

U.S. Pat. No. 7,002,670 B2 discloses an optical sensor for measuring a particular chemical component in a solution with a plurality of absorbing chemical components. In particular, a method for measuring creatinine in spent dialysate before, during and after a dialysis treatment as well as a device (optical sensor) for this purpose are described. The quantitative determination of creatinine is performed in a multi-step procedure. In a first step the total absorption of the spent dialysate including the absorption of creatinine is detected. Then, the absorption of creatinine is selectively removed from the ensemble of absorbing substances in that biocatalytic processes (enzymes) are used in a reactor. Subsequently, a second absorption signal is detected, wherein the difference between the first and the second absorption signals is proportional to the concentration of creatinine.

A disadvantage of this state of the art consists in that enzymes are used. Enzymes have the disadvantage that, inter alia, their dosage and their storage/durability have to be monitored.

DE 26 58 101 A1 discloses a method for the concentration of low-dimensional compounds in complex media, preferably in the case of medical treatments. It describes a method producing a smaller portion of a complex medium with the aid of dialysis. The measurement of the content of a substance is then performed in the smaller portion, i.e. in the dialysate. The measurement in the dialysate is in particular performed after or in connection with a chemical modification of the low-molecular compound with the aid of one or a plurality of enzymes.

A problem with this state of the art also consists in that enzymes with the afore-mentioned disadvantages are used for measurement.

US 2008/0015434 A1 discloses a method by which it is possible to determine the ejection fraction of a patient's heart in a non-invasive manner during a hemodialysis therapy. For this purpose, a fluorescent colorant is introduced into the patient's cardiovascular system. The fluorescent colorant is excited by a radiation source at a first wavelength. The emitted light is detected at a second wavelength which differs from the first wavelength.

WO 2009/071102 A1 discloses a device comprising a cuvette for storing a biologic fluid. The device comprises an optical module for the spectroscopic examination of the biologic fluid which consists of a light source whose light is guided into the cuvette. The light from the cuvette is subsequently detected by a detector.

WO 2010/024963 A1 discloses a system for the preparation of dialysate comprising a purification medium for water, a device for pumping or measuring water, a heating device for heating water, a chamber for mixing water and a concentrate for producing fresh dialysate, a filter for filtering fresh dialysate, and a microelectromechanical sensor (MEMS).

In this state of the art a purification medium or a filter is required, so that the effort with respect to apparatus is relatively large.

DE 10 2011 101 193 A1 discloses a method for the photometric determination of the contents of urea and creatinine in a fluid. UV radiation at three wavelengths in the wavelength range between 235 nm and 300 nm is irradiated into the fluid and the radiation absorption in the fluid is measured at the predetermined wavelengths. A first one of the wavelength ranges is in a partial range between 235 nm and 250 nm, a second one in a second partial range between 255 nm and 270 nm, and a third one in a third partial range between 280 nm and 300 nm. The contents of urea and creatinine and optionally the content of a third component are calculated from the measurement results.

EP 1 083 948 B1 describes the determination of the content of one or a plurality of combined substances. In this process, a spectroscopic value is multiplied with the flow of the examined dialysate.

GB 2 390 420 A describes a method for determining the concentration of one or a plurality of substances in a sample. For this purpose, a derivation algorithm of a second device (e.g. spectrometer) prepared for a sample is transferred to a first device (e.g. sensor). This enables the first device to calculate the content of a substance by the measurement of absorbance values at different wavelengths.

SUMMARY OF THE INVENTION

In this state of the art standard spectrums or curves of second devices are a precondition for calculating the concentration.

Thus, any state of the art explained above has at least one specific disadvantage. In particular, however, the use of enzymes for the determination of the content of creatinine is deemed to be a disadvantage since they cause storage costs, their durability has to be monitored, the dosage has to be performed exactly, and quantifiable measurements are possible to a limited extent only.

In view of the afore-explained problems it is the basic object of the present invention to provide an apparatus, e.g. an extracorporeal body fluid purification apparatus, preferably a dialysis apparatus, and an analysis/measurement method and/or apparatus control method by which it is possible to determine a quality measure for the dialysis, preferably the concentration of selected toxic substances, and/or to determine a removed total quantity of uremic toxins during a dialysis (i.e. determine a clearance during a dialysis by an extracorporeal purification apparatus), all that without the use of enzymatic methods, Jaffe methods or other reagents not occurring during a usual HD dialysis therapy. It is in particular an object of the present invention to provide an apparatus and an (apparatus control) method for the quantitative concentration determination of selected uremic toxins in a fluid, for instance, a fluid excreted/extracted from the body (such as urine, blood, plasma, etc.) or an extracorporeal blood purification fluid, on the basis of which the quality measure for the body fluid purification, preferably the concentration of selected toxic substances, can then be determined and/or a removed total quantity of uremic toxins during a body fluid purification can be determined (for instance, the clearance).

This object is solved by apparatus and methods with the features described herein, e.g., for determining the quality measure pursuant to the foregoing definition.

The invention is substantially based on the quantitative determination of the concentration of a selected and/or selectable filtered/dialyzed (toxic) substance, e.g. a uremic toxin such as creatinine and/or uric acid in a fluid excreted/extracted from the body or a spent dialysate with an optical sensor. For this purpose, for instance, during an extracorporeal blood treatment/blood purification the pH value of the (spent) dialysate (or the excreted/extracted body fluid) is modified and an extinction signal is detected continuously or respectively for the different pH values. This signal is then used as an indicator of the selected substance dissolved in the fluid/dialysate. By the processing/comparing of the determined extinction signals in the fluid/dialysate, for instance, at a first pH value and at a second pH value, a processing/comparing signal is generated which depends on the concentration of the selected substance to be examined. The processing/comparing signal is in particular a difference signal formed by the subtraction of the spectrums taken at different pH values.

In detail, an apparatus is provided for the quantitative concentration determination of selected or selectable substances, such as uremic toxins in a fluid, preferably a fluid excreted/extracted from the body or an extracorporeal blood purification fluid, comprising:

an optical absorption sensor adapted to detect at least one first extinction signal of the fluid excreted/extracted from the body or the spent dialysate, at at least one predetermined or adjustable analysis wavelength at a defined, preferably adjustable first pH value of the fluid excreted/extracted from the body or the spent dialysate, a pH adjusting/changing device adapted to adjust a second pH value of the fluid excreted/extracted from the body or the spent dialysate which differs from the first pH value, the optical absorption sensor adapted to detect at least one second extinction signal of the fluid excreted/extracted from the body or the spent dialysate at the at least one equal analysis wavelength at the second pH value, a signal processing device adapted to process, preferably compare, the two extinction signals at the first and the second pH values, and a determination device adapted to determine an absolute concentration of at least one selected or selectable substance, such as uremic toxins, in the fluid excreted/extracted from the body or the spent dialysate on the basis of the result of the signal processing device.

Thus, the invention makes use of the dependence of the absorption properties of a selected and/or selectable substance on the pH value of the fluid in which the substance is dissolved so as to determine the concentration thereof doubtlessly or with utmost exactness (by calculation or with a table).

The apparatus preferably has an analysis wavelength adjusting device adapted to adjust the analysis wavelength to a value at which the selected and/or selectable substance changes its absorption property if the pH value changes.

Further preferably the analysis wavelength adjusting device is adapted to adjust the analysis wavelength to a value at which a non-selected substance does not or negligibly change its absorption property with respect to the signal processing device if the pH value changes. Thus, it is not necessary to change the analysis wavelength, for which purpose a comparatively expensive multi-wave absorption sensor would be required, but a comparatively cheap single-wave absorption sensor may be used, in particular a single-wavelength sensor, wherein the wavelength is correspondingly predetermined by the light source used;

Preferably, the apparatus is adapted to analyze a dialysate, blood, plasma, urine or similar medical/biological or other solvents with the optical absorption sensor.

Further preferably, the pH adjusting/changing device is adapted to adjust the first pH value to (approximately) 7.3. This value corresponds roughly to that of blood and can generally be found in conventional dialysates.

It would further be of advantage if the pH adjusting/changing device changed the pH value of the fluid excreted/extracted from the body or the dialysate by using an electrolytic method with an electrolytic cell (13) or by adding acids, bases and gases, such as $CO_2$. This enables, in accordance with a further advantageous embodiment of the invention, that the pH adjusting/changing device is adapted to determine at least the first and/or the second pH value with the respective mixing ratio between the fluid excreted/extracted from the body or the dialysate and an additive changing the pH value.

It is further of advantage if, in the case of overlapping absorption bands of the selected substance and at least one further, non-selected substance, the absorption sensor could operate at an isosbestic wavelength of the non-selected substance. In this manner it is possible to avoid or reduce measurement distortions.

For instance, the analysis wavelength is approximately 254 nm for the analysis of creatinine, corresponding to the isosbestic point of uric acid and/or approximately 300 nm for the analysis of uric acid. In reality, for the analysis of creatinine a per se known light source with a known light wavelength of 253.7 nm might, for instance, be used, wherein the sensor used measures light with a wavelength of approximately 254 nm (concretely between approximately 253 nm and approximately 255 nm). Such deviations from the technical teaching described corresponding to the light sources and sensors usable in reality possibly still make use of the principle of the present invention and are therefore intended to be comprised by the present disclosure.

The apparatus control method according to aspects of the invention for the quantitative concentration determination of selected or selectable substances, such as uremic toxins in a fluid, preferably dissolved in a fluid excreted/extracted from the body or an extracorporeal blood purification fluid, and preferably for the determination of a quality measure for the dialysis, preferably the concentration of selected toxic substances, and/or for the determination of a removed total quantity of uremic toxins during a dialysis with a dialysis apparatus, comprises the steps of:

detecting, by an optical absorption sensor, at least one first extinction signal of a fluid excreted/extracted from the body or a spent dialysate, at at least one predetermined or adjustable analysis wavelength at a first, preferably preadjusted first pH value of the fluid excreted/extracted from the body or the spent dialysate, adjusting, by a pH adjusting device, a second pH value of the fluid excreted/extracted from the body or the spent dialysate which differs from the first pH value, detecting, by the absorption sensor, at least one second extinction signal of the fluid excreted/extracted from the body or the spent dialysate at the at least one predetermined or selected analysis wavelength at the second pH value, processing the two extinction signals at the first and the second pH values preferably by calculating the difference and determining, preferably by calculating or tabular determination, an absolute concentration of at least one selected substance dissolved in the fluid excreted/extracted from the body or the spent dialysate, on the basis of the result of processing.

Preferably, in the case of overlapping absorption bands of the selected substance and at least one further, non-selected substance, the at least one predetermined analysis wavelength is determined as an isosbestic analysis wavelength with respect to the non-selected substance.

Further preferably, the at least one predetermined analysis wavelength is adjusted to approximately 254 nm for the analysis of creatinine, corresponding to the isosbestic point of uric acid and/or approximately 300 nm for the analysis of uric acid.

The method according to aspects of the invention for determining the selected substance and possibly for determining the quality measure for the dialysis, preferably the concentration of selected toxic substances, and/or for determining a removed total quantity of uremic toxins during a dialysis (clearance of the kidney or of the dialysis apparatus in dialysis) in other words comprises the steps of:

detecting, by an (optical) absorption sensor, at least one first extinction signal of the fluid excreted/extracted from the body or a spent dialysate, at at least one predetermined analysis wavelength at a defined, possibly preadjusted first pH value of the fluid/dialysate, changing, by a pH adjusting/changing device (9; 13; 15), the first pH value to a differing second pH value of the fluid excreted/extracted from the body or the dialysate, detecting, by the absorption sensor, at least one second extinction signal of the fluid excreted/extracted from the body or the spent dialysate at the at least one predetermined analysis wavelength at the second pH value, processing/comparing the at least two extinction signals at least at the first and the second pH values and determining an absolute concentration of at least one selected substance dissolved in the fluid excreted/extracted from the body (urine, blood, plasma, etc.) or in the dialysate.

Thus, the control method according to aspects of the invention can be circumscribed more concretely as follows, wherein it has to be pointed out in this place that both the apparatus and the method cannot just be applied in a patient's dialysis, but on principle also in other medical or non-medical processes for determining the concentration of substances dissolved in fluid:

In a first step there is first of all selected which (toxic) substance (the concentration thereof), e.g. the creatinine concentration, is to be examined.

In a second step a wavelength range is defined in which the (toxic) substance to be examined exhibits an absorption/absorbance property which can be detected with a sensor (optically).

In a third step there is examined whether—and in the affirmative—with which other (toxic) substance(s) an overlapping of the respective absorption bands (wavelengths) exists, whereby an allocation of a current absorption signal obtained by a sensor to a corresponding concentration of the (toxic) substance to be examined is aggravated/rendered impossible.

In a fourth step the wavelength to be used is determined in an isosbestic point of the other non-selected (toxic) substance(s), so that in the case of a pH change of the fluid excreted/extracted from the body or the dialysate only the selected (toxic) substance to be examined changes its absorption property (and the other, non-selected (toxic) substances do not/slightly).

In a fifth step the fluid excreted/extracted from the body/the spent dialysate is measured with an (optical) sensor (UV sensor) which is adjusted to the wavelength determined in step four, at least at a first (selected or predetermined) pH value of the fluid excreted/extracted from the body or the dialysate, so as to obtain a first measurement value.

In a sixth step the fluid excreted/extracted from the body/the spent dialysate is measured with an (optical) sensor (UV sensor) which is adjusted to the wavelength determined in step four, at least at a second (selected or predetermined) pH value of the fluid excreted/extracted from the body/the dialysate, so as to obtain at least one second measurement value (or continuous measurement).

In a seventh step a processing, preferably difference, signal (proportional to the concentration of the (toxic) substance to be examined) is formed between the different measurement values.

In an eighth step the processing signal is finally allocated to a corresponding concentration of the selected substance.

Preferred embodiments of the method according to aspects of the invention comprise as one feature or as a combination of several features that:

the at least one predetermined analysis/measurement wavelength is an isosbestic analysis wavelength at which the extinction signal of a non-searched substance with overlapping pH-specific absorption properties is independent of the pH value;

the at least one predetermined analysis wavelength is 254 nm, corresponding to the isosbestic point of uric acid;

the pH value of the dialysate at the outlet side is changed by electrolysis, by the adding of an acid, a base or a gas, in particular $CO_2$;

a plurality of different analysis wavelengths are used for the determination of different substances.

In this place, the following constellations are mentioned as examples:

If preferably the concentration of creatinine is to be analyzed/measured, the measurement wavelength of the optical sensor should, for instance, be adjusted to 254 nm since the share of uric acid is there (substantially) harmless for the measurement result because this wavelength constitutes the isosbestic point of the uric acid. If the pH value of the fluid excreted/extracted from the body/the dialysate is changed at this wavelength, the absorption property (absorbance) of creatinine will change, not, however, that of uric acid. Thus, the creatinine concentration can be detected and determined. If preferably the concentration of uric acid is to be analyzed/measured, the measurement wavelength of the optical sensor should, for instance, be adjusted to 300 nm since the share of creatinine is there harmless for the measurement result.

The corresponding apparatus according to aspects of the invention for the quantitative concentration determination of selected uremic toxins in a fluid, for instance, a fluid excreted from the body (such as urine) or an extracorporeal blood purification fluid, for instance, a dialysis apparatus, comprises:

an absorption sensor to detect at least one first extinction signal of the fluid excreted from the body or the spent dialysate at at least one predetermined analysis wavelength at a first pH value defined by the fluid excreted from the body or the dialysate, and possibly being adjustable, a pH adjusting device to adjust a second pH value which differs from the first pH value of the fluid excreted from the body or the spent dialysate, the optical absorption sensor to detect at least one second extinction signal of the fluid excreted from the body or the spent dialysate at the at least one predetermined analysis wavelength as a function of the second pH value, a comparing device to compare the two extinction signals at the first and the second pH values, and a determination device to determine an absolute concentration of at least one substance dissolved in the fluid excreted from the body/the dialysate on the basis of the result of the comparing device.

An advantage of the invention consists in that an optical evaluation can easily be integrated in a flow system and offers high measurement accuracy. Thus, when measuring, for instance, creatinine with the aid of an optical sensor, the invention can do without enzymes which are expensive, difficult to dose, and have short durability. The quantitative measurement, for instance, of creatinine or uric acid is also enabled in the course of a dialysis therapy. The invention also enables the use of a cost-efficient sensor which is designed for one wavelength. It is in particular possible to calculate a creatinine concentration with an optical sensor in a very small wavelength range from an extinction signal prevailing there.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

The invention relates to the changing of the absorption properties of a selection of substances, inter alia, creatinine and/or uric acid, with the changing of the pH value, for instance, of spent dialysate. From the measurement of the absorption at least at two different pH values a difference signal is generated. This difference signal comprises only contributions of fewer substances than the original absorption signal, so that the determination of the concentration of individual substances is facilitated. In particular, the sensor parameters are chosen such that the creatinine concentration in the spent dialysate can be determined.

Creatinine is not the only substance to experience a change of the absorption properties by the change of the pH value. The number of uremic toxins exihibiting a strong change of the absorption properties is indeed distinctly lower than the group of all absorbing substances in spent dialysate, which strongly facilitates the allocation. However, there are uremic toxins such as, for instance, uric acid which change their absorption properties in the same pH and wavelength ranges as creatinine.

In order to simplify the difference signals, measurements are preferably performed in isosbestic points. Isosbestic points are wavelength positions at which the value of the extinction before and after the change of the pH value does not change, although at other wavelengths the absorption of the corresponding substance absolutely depends on the pH value. Since an isosbestic point of uric acid lies in the wavelength range in which the difference signal of creatinine is distinct, the difference signal may be allocated completely to creatinine there.

A first embodiment of the dialysis apparatus according to aspects of the invention which is described by way of example provides that a first pump supplies fresh dialysate to the inlet of a dialyzer. In the dialyzer, uremic toxins are transferred from the blood of the patient into the dialysate. Consequently, the fresh dialysate becomes spent dialysate. The spent dialysate leaves the dialyzer at its outlet and is transported within a hose system at the dialysate side in the direction of rejection. In this process, the spent dialysate may pass different devices such as, for instance, a balance chamber or an optional mixing chamber. It is decisive that, at a point in time prior to the changing of the pH value, it flows past an optical sensor which is capable of detecting/detects at least one first extinction signal of spent dialysate. In a second step a second pump introduces a substance changing the pH value into the spent dialysate in front of the optical sensor. The connected optical sensor (absorption sensor) then supplies at least one second extinction signal at a second pH value differing from the first pH value. Then, the concentration of a substance can be determined, for instance, by calculation or with a table from the at least two extinction values obtained.

Figure 1:
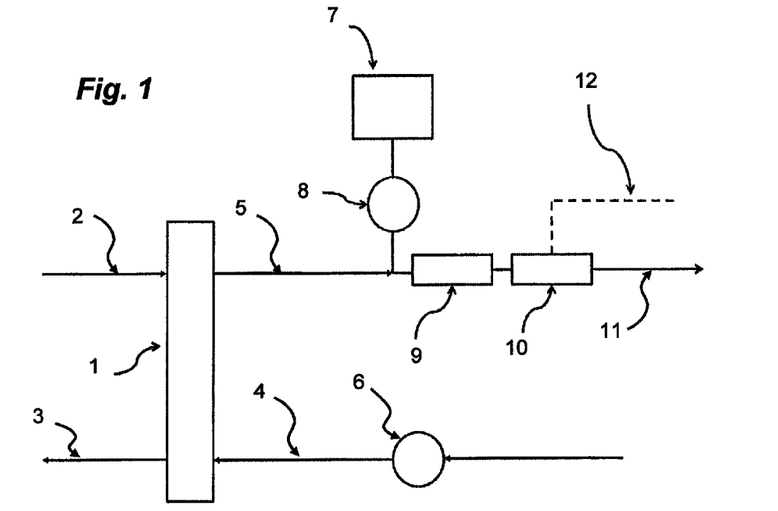
FIG. 1 illustrates schematically a first embodiment of the dialysis apparatus according to aspects of the invention.

This is illustrated in detail in FIG. 1. FIG. 1 illustrates schematically a dialyzer 1 with a blood inlet 2 and a blood outlet 3 in a first embodiment of the invention. Through the blood in let 2 blood is guided from the circulation of the patient (not illustrated) into the dialyzer 1 where it gives off, caused by diffusion and/or convection, particular substances (uremic toxins) in the blood of the patient through a membrane (not illustrated) to a dialysate. The dialysate is pumped into the dialyzer through a dialysate inlet 4 and is removed again through a dialysate outlet 5. For this purpose a dialysate pump 6 is provided.

In a dialysis treatment it is of advantage and possibly necessary that the concentration of the substances passed over from the blood to the dialysate is monitored. For this purpose, the invention makes use of the change of optical parameters associated with the change of the pH value of the dialysate at the outlet side, i.e. the dialysate loaded with uremic toxins, for instance due to changes of absorption properties of particular substances dissolved therein. In order to be able to manipulate the pH value of the dialysate, a substance container 7 with a substance changing the pH value is preferably provided. A substance pump 8 admixes the substance to the dialysate at the outlet side. This is performed as an example either directly or in an optional mixing path 9 of the dialysis apparatus according to aspects of the invention, with other measures also being possible.

The change of the optical properties of the spent dialysate manipulated this way is detected in an optical sensor 10. The optical sensor 10 is in particular an absorption or extinction sensor. Subsequently, the spent dialysate is discharged in a so-called rejection 11. The data at least from the optical sensor 10 are output via a communication interface 12 to a processing unit (not illustrated) for further processing.

In order to determine, for instance, a quality measure for the dialysis, preferably the concentration of selected toxic substances, and/or a removed total quantity of uremic toxins during a dialysis (clearance in a dialysis) and to thus be able to assess the quality and/or the progress of the dialysis, at least one pH value of the dialysate at the outlet side is adjusted by the pH adjusting device which comprises an optional mixing path 9 in the embodiment pursuant to FIG. 1. The extinction signal of the dialysate at the outlet side is detected and evaluated in the optical sensor 10. The embodiment is not only restricted to one absorption measurement and one pH value of the dialysate. The absorption measurement may as well be performed at several analysis wavelengths of the optical sensor 10, and the absorption measurement is performed for several pH values of the dialysate. The extinction signals at one wavelength are compared for each adjusted pH value, and an absolute concentration of a substance dissolved in the dialysate is determined from the comparison. The comparison comprises in particular a subtraction of the absorption values from each other. Alternatively, a quotient of the absorption values may be formed instead of a difference.

The above proceeding may optionally be modified in the following manner. A first pump supplies fresh dialysate to the inlet of the dialyzer. In the dialyzer uremic toxins from the blood of the patient are transferred into the dialysate. Consequently, the fresh dialysate becomes spent dialysate. The spent dialysate leaves the dialyzer at its outlet and is transported within a hose system in the direction of rejection. At an optional three-way valve the direction of the flow is determined. At a first point in time the valve is controlled such that spent dialysate is bypassed into a container. The fluid exiting from the container flows through an optical sensor receiving a first extinction signal. Then, the three-way valve is switched, which results in that the flow of spent dialysate is guided to the rejection directly. In the next step a pump conveys a fluid changing the pH value into the container. Then, the pump transports the fluid with the changed pH value from the container to the optical sensor which records a second extinction signal. The concentration of a substance is determined from the two values obtained.

The change of the pH value may also be performed in different ways, for instance, by the change of the composition of the dialysate as such. In this case the container with the substance changing the pH value would be omitted and the substance changing the pH value would be taken along in the flow of the spent dialysate as a bolus instead. This may be achieved in different ways such as e.g. in the bypass mode (not illustrated) in which the dialysate outlet and the dialysate inlet are directly connected with each other. The bolus may then be selected from the flow of the dialysate by an appropriate switching of the optional three-way valve and may be bypassed to the container for adapting the pH value. The fluid produced this way in turn has a second extinction signal generated at the optical sensor which is referred to for the calculation of a concentration.

Figure 2:
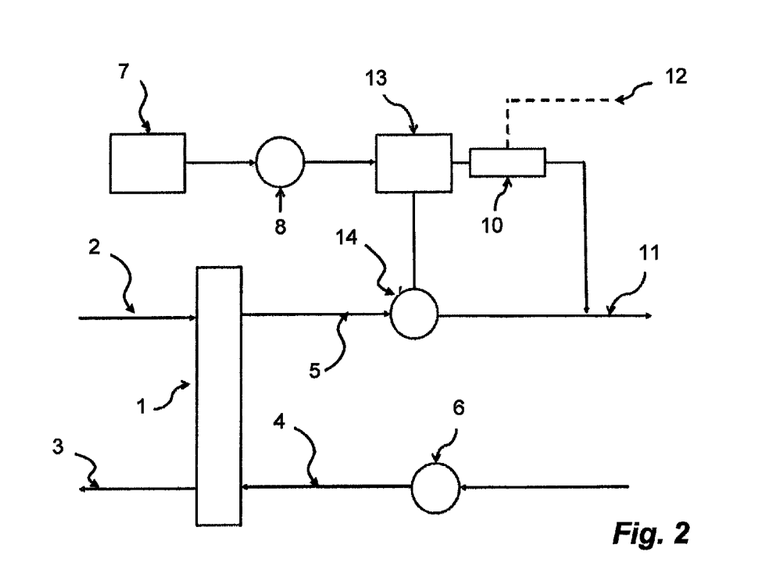
FIG. 2 illustrates schematically a second embodiment of the dialysis apparatus according to aspects of the invention.

The corresponding apparatus is illustrated in FIG. 2. Through the blood inlet 2 blood is guided from the circulation of the patient (not illustrated) into the dialyzer 1 where it gives off, caused by diffusion and/or convection, particular substances through a membrane (not illustrated) to a dialysate. The dialysate is pumped into the dialyzer through a dialysate inlet 4 and is removed again through a dialysate outlet 5. For this purpose a dialysate pump 6 is preferably provided.

A substance container 7 supplies, via a substance pump 8, an adaptation container 13 with a substance changing the pH value for the adaptation of the pH value of its content. The optical properties of the content of the adaptation container 13 are detected in an optical sensor 10 and are output via a communication interface 12 to a processing unit (not illustrated) for further processing. The dialysate is discharged in the rejection 11.

The changing supply of the adaptation container 13 with spent dialysate, the draining of the adaptation container and the discharging of its content to the rejection is performed with a three-way valve 14. Thus, the embodiment of the dialysis apparatus according to aspects of the invention is designed to be controlled in a particularly simple manner. Such a three-way valve moreover enables the implementation of the bypass mode (not illustrated) in a simple manner, wherein the dialysate outlet and the dialysate inlet are directly connected with each other.

A further modification of the construction pursuant to FIGS. 1 and/or 2 consists in that the change of the pH value is performed with electrolysis. In this approach, the construction of the dialysis apparatus according to aspects of the invention is similar to the above embodiment pursuant to FIG. 2 until the spent dialysate reaches the three-way valve 14. There, the spent dialysate is conveyed into a container which is simultaneously an electrolysis cell. The absorption sensor detects a first extinction signal before the change of the pH value and a second extinction signal after a particular pH value was adjusted in the electrolysis cell. The concentration of the desired substance is determined from the extinction signals.

Figure 3:
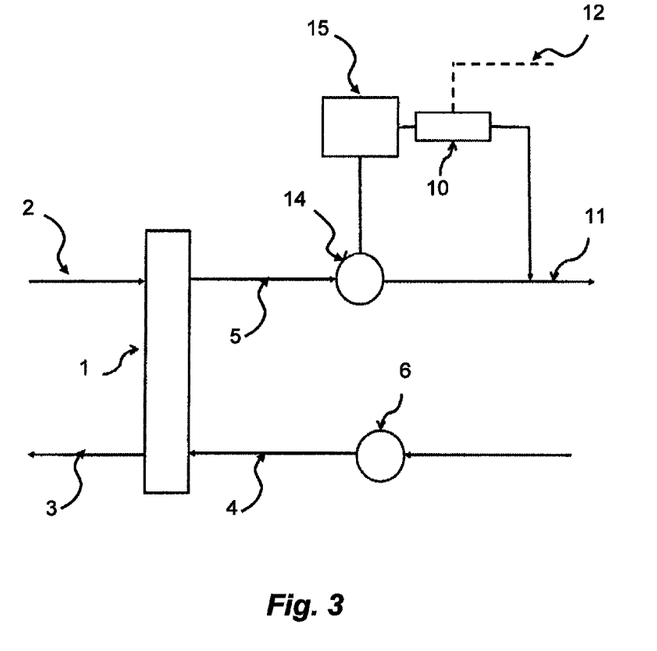
FIG. 3 illustrates schematically a third embodiment of the dialysis apparatus according to aspects of the invention.

The construction in FIG. 3 in which the pH value is changed with electrolysis consequently comprises, instead of storage containers for substances changing the pH value, an electrolysis container 15 serving to adapt the pH value with electrolysis. Thus, the embodiment pursuant to FIG. 3 has a particularly compact structure.

The determination of the quality measure for the dialysis, preferably the concentration of selected substances, and/or the removed total quantity of uremic toxins during a dialysis (clearance) is based on a particular substance dissolved in the blood and/or in the dialysate. Accordingly, the optical sensor is adjusted to this substance. For the measurement of creatinine by an apparatus according to FIG. 1, 2 or 3, the sensor wavelength for the measurement of creatinine concentrations is adjusted to approximately 254 nm. By the selection of this wavelength it is possible to neglect uric acid during the calculation of the creatinine concentrations.

A prerequisite for the measurement with this wavelength is a preferably symmetrical light source with the central wavelength of 254 nm+/−5 nm. This may be achieved by the use of LEDs or lamps. In particular Hg low pressure vapor lamps are characterized by a narrow-band line of 253.7 nm and thus constitute, in combination with appropriate filters, the optimum light source for the determination of the creatinine extinction. Instead of a symmetrical light source it is also possible to use broad-band light sources in combination with appropriately narrow-band optical filters and/or monochromators.

The invention is not restricted to the measurement of creatinine. Thus, uric acid may also be detected with an apparatus according to FIG. 1, 2 or 3. The pH value-dependent shifting of the extinction of uric acid may be observed in many wave length ranges. The range between 290 nm and 310 nm is particularly well suited for the differentiation from other substances in the spent dialysate. The range between 260 nm and 290 nm is also possible. For the examination of the content of uric acid in the dialysate a light source may be used, e.g. an appropriate LED having a half-power width of maximally 10 nm.

The extinction measurements of creatinine and uric acid will be explained in the following with extinction spectrums obtained pursuant to the method according to aspects of the invention.

Figure 4:
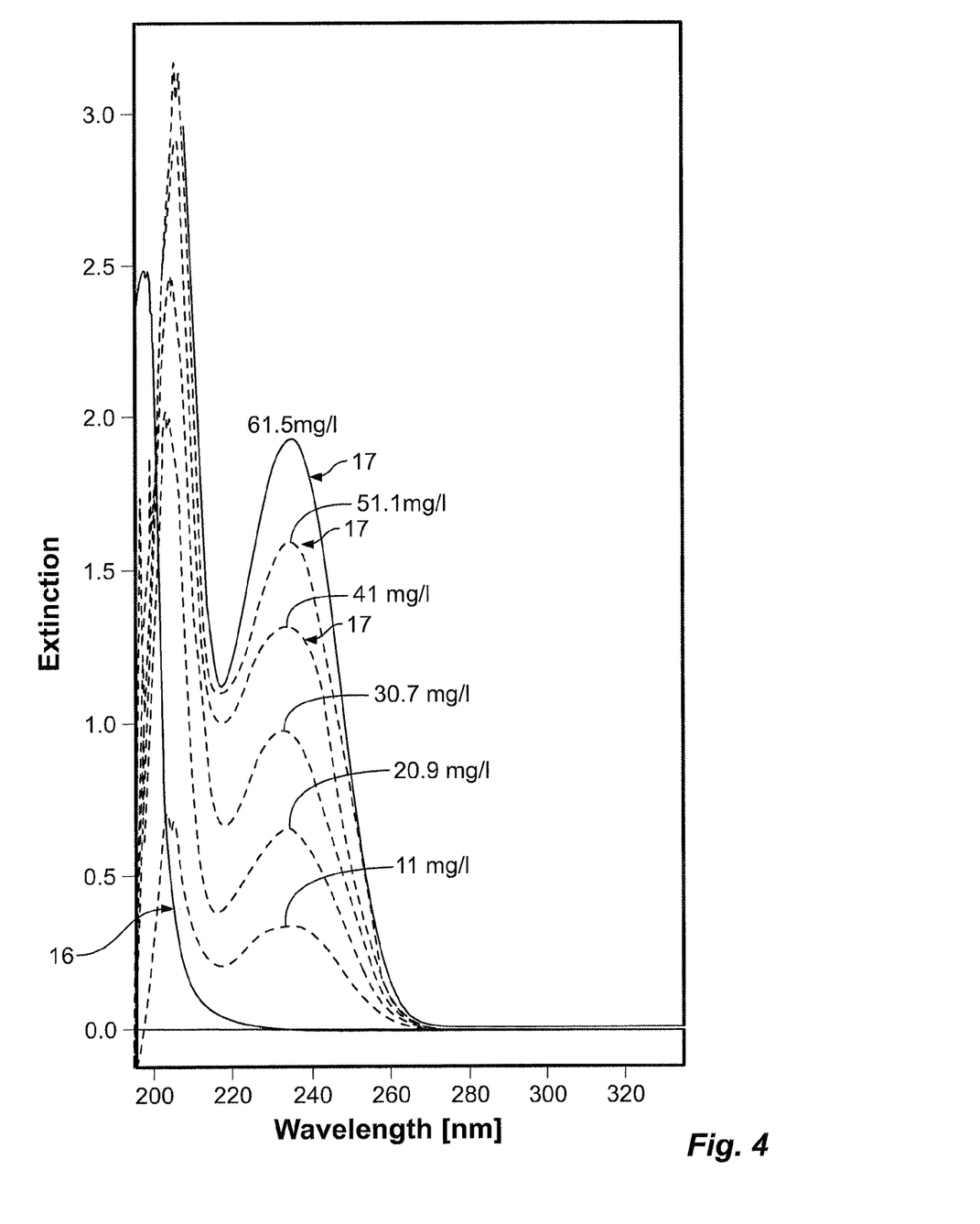
FIG. 4 illustrates an extinction spectrum of unspent dialysate in comparison to the extinction spectrum of creatinine.

Uremic toxins absorb light in the range between 190 nm-400 nm. FIG. 4 illustrates an extinction spectrum 17 of dialysate at the outlet side for a plurality of different concentration values of creatinine. For comparison, FIG. 4 illustrates an extinction spectrum 16 for the dialysate at the inlet side in the same range.

In practice, the extinction spectrum 17 of spent dialysate is, however, composed of more than just the creatinine spectrum. Overlappings of extinction spectrums of other uremic toxins aggravate the unambiguous allocation of an extinction to individual uremic toxins such as, for instance, creatinine or uric acid.

Figure 5:
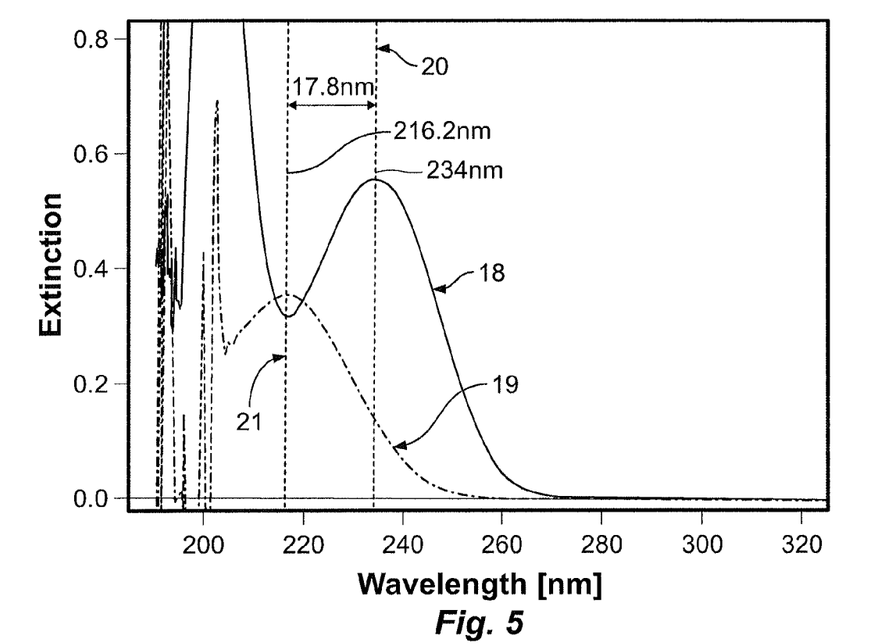
FIG. 5 illustrates the extinction behavior of creatinine at a pH value of the dialysate of approx. 7.3 and/or approx. 4.

Moreover, the form of the spectrum is also changed by the adjusted pH value. This means that creatinine, dissolved in dialysate, has an extinction spectrum 17 which depends on the pH value of the dialysate. FIG. 5 illustrates an extinction 18 of creatinine at a pH value of the dialysate of ~7.3 (continuous line) and an extinction 19 of creatinine at a pH value of the dialysate of ~4 (dashed line). The extinction 18 of creatinine at a pH value of the dialysate of ~7.3 has a local long-wave maximum 20 at approximately 234 nm, the extinction 19 of creatinine at a pH value of the dialysate of approximately 4 has a local long-wave maximum 21 at approximately 216 nm. The wavelengths of the maxima 20, 21 of the extinction spectrum are illustrated as dashed vertical lines. The distance of the maxima 20 and 21 for the pH value of 7.3 and/or approximately 4 is approximately 18 nm. Simultaneously with the pH value the extinction in the respective maximum decreases by about 40%.

A change of the extinction as a function of the pH value does not only occur with creatinine. From a large number of absorbing substances which may occur in spent dialysate, however, only one further uremic toxin has been identified so far whose extinction signal changes in a comparable manner as creatinine does as a function of the pH value, namely uric acid.

The concentration measurement of these two substances is performed in accordance with the invention by the determination of the difference spectrums at at least two different pH values and/or extinction values. Basically, all wavelength positions at which the extinction difference is larger than zero may be used for calculating the substance-specific extinction. Actually, the selection of the wave length position depends on the availability of appropriate light sources. Preferably, a sensor operating at approximately 254 nm in the isosbestic point of uric acid is used for determining the extinction of creatinine. Since the extinction difference of uric acid is zero at the isosbestic point of uric acid, the one of creatinine, however, is not, the allocation of the extinction to the creatinine concentration is possible.

Figure 6:
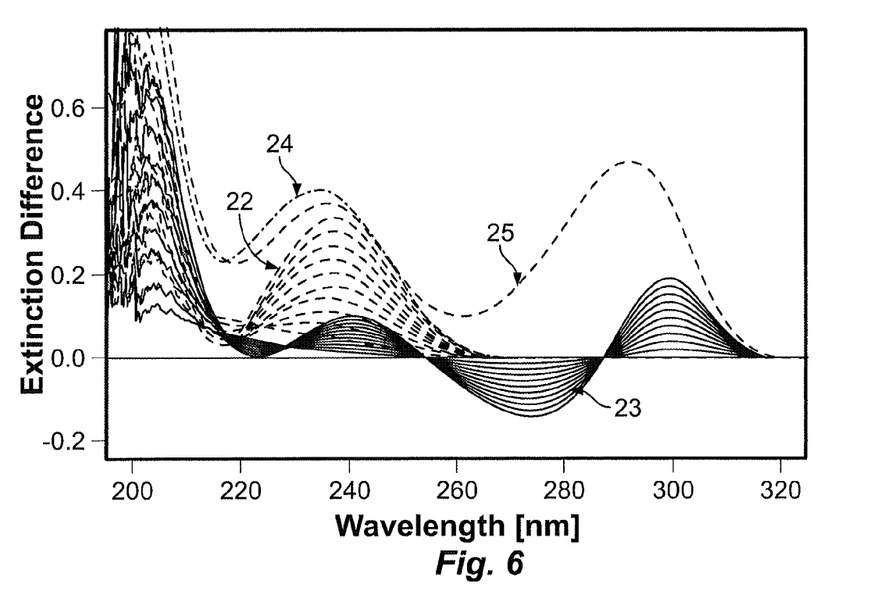
FIG. 6 illustrates difference extinction spectrums of uric acid and creatinine as a serial dilution as well as the extinction spectrums at a pH value of 7.3.

A set of difference spectrums for creatinine and uric acid is illustrated in FIG. 6. The set of curves designated with 22 is a difference spectrum of creatinine in a plurality of degrees of dilution, and the set of curves designated with 23 is a difference spectrum of uric acid in a plurality of degrees of dilution. Additionally, an extinction spectrum 24 of creatinine at pH value 7.3 and an extinction spectrum 25 of uric acid at pH value 7.3 are illustrated.

The invention can be summarized as follows. The concentration of selected substances in various biological fluids is determined by the pH-dependent change of the extinction. The preferably biological fluids to be examined may be different products of the human organism. The method is conceived for applications in blood, plasma, urine and fresh/spent dialysate, but may also be used in other optically clear solvents for the determination of absorbing substances. In particular, the measurement of the extinctions of a biological fluid being in flow is possible, wherein the measurement takes place during a HD therapy. It is further conceivable not to perform the measurements at two different pH values only, but at a plurality of different pH values or even continuously in the course of a pH change.

The concentration is substantially determined from the detection of two extinction signals. Extinction means the decadic absorption measure which is detected by an optical sensor in this invention. The extinction signals are received at different times at different pH values of the biological fluid, and concentrations of the desired substance are determined from them.

The pH value of the biological fluid may be changed in different manners, e.g. by electrolytic methods or by the addition of acids, bases and gases such as $CO_2$. In dialysis, acid hemodialysis concentrate and citric acid come into question as acids which are dispensed into the flow by an appropriate device and thus contribute to the change of the pH value. Alternatively, the pH value is adjusted in a manner preferred according to aspects of the invention by a mixing ratio. This means that only the ratio between the spent dialysate and the added acid has to be known to adjust the desired pH value.

With the optical sensor different substances are detected depending on the operating wavelength. The isosbestic point of uric acid at 254 nm is particularly well suited for the optical evidencing of creatinine, independently of other available interfering substances. Additionally, uric acid in the range of approximately 300 nm, for instance, is determined in the same manner.

The spent dialysate flows in a first step through the optical sensor which detects a first extinction signal of the dialysate.

Subsequently, a pump supplies acid concentrate from a container into the spent dialysate and thus changes the pH value of the solution. For better mixing, a mixing path may optionally be provided. The controlling of the pump is performed by the sensor itself or by a control device (not illustrated). The sensor also detects the second extinction signal of the dialysate. From the two extinction signals the sensor determines a corresponding concentration of creatinine and outputs same.

For determining a substance in a fluid excreted/extracted from the body or the spent dialysate, and in particular for determining a quality measure for the dialysis, preferably the concentration of selected toxic substances, and/or for determining the removed total quantity of uremic toxins during a dialysis (clearance in dialysis) with a dialysis apparatus, the analysis apparatus in accordance with the invention as well as the apparatus control method used comprise the following:

detecting, by an absorption sensor (10), at least one first extinction signal of the fluid excreted/extracted from the body or the spent dialysate, at at least one predetermined analysis wavelength at a defined, possibly preadjustable first pH value of the fluid, adjusting, by a pH adjusting device (9; 13; 15), a second pH value of the fluid which differs from the first pH value, detecting, by the absorption sensor (10), at least one second extinction signal of the fluid at the at least one predetermined analysis wavelength at the second pH value, processing/comparing the two extinction signals for the first and the second pH values and determining an absolute concentration of the substance dissolved in the fluid.

The invention claimed is:

1. An apparatus for quantitative concentration determination of selected or selectable substances such as uremic toxins in a fluid, comprising:
   an optical absorption sensor adapted to detect at least one first extinction signal of the fluid at at least one analysis wavelength at a first pH value of the fluid;
   a pH device adapted to adjust the fluid to a second pH value that differs from the first pH value;
   the optical absorption sensor further adapted to detect at least one second extinction signal of the fluid at the at least one analysis wavelength at the second pH value;
   a signal processing device adapted to process the two extinction signals at the first and the second pH values to obtain a result;
   a determination device adapted to determine at least one of an absolute concentration or a signal proportional to the concentration of at least one selected or selectable substance in the fluid on the basis of the result of the signal processing device; and
   an analysis wavelength adjusting device adapted to adjust the analysis wavelength to a value at which the selected or selectable substance changes its absorption property if the pH value changes.

2. The apparatus of claim 1, wherein the fluid is excreted from a body, is extracted from the body, or is an extracorporeal blood purification fluid.

3. The apparatus according to claim 1, wherein the analysis wavelength adjusting device is adapted to adjust the analysis wavelength to a value at which a non-selected substance does not or negligibly change its absorption property with respect to the signal processing device if the pH value is changed.

4. The apparatus according to claim 1, wherein the apparatus is adapted to analyze a dialysate, blood, plasma, urine or similar medical/biological solvents by means of the optical absorption sensor.

5. The apparatus according to claim 1, wherein the optical absorption sensor is a single wavelength sensor using only a signal with a single predefined or selectable analysis wavelength in the scope of an analysis process.

6. The apparatus according to claim 1, wherein the pH device is adapted to adjust the first pH value to approximately 7.3.

7. The apparatus according to claim 1, wherein the pH device changes the pH value of the fluid by using an electrolytic method by means of an electrolytic cell or by adding acids, bases and gases, such as $CO_2$.

8. The apparatus according to claim 7, wherein the pH device is adapted to determine at least one of the first or the second pH value by means of a respective mixing ratio between the fluid and an additive changing the at least one pH value.

9. The apparatus according to claim 1, wherein, in the case of overlapping absorption bands of the selected substance and at least one further, non-selected substance, the absorption sensor operates at an isosbestic wavelength of the non-selected substance.

10. The apparatus according to claim 9, wherein the analysis wavelength is at least one of approximately 254 nm for the analysis of creatinine, corresponding to the isosbestic point of uric acid or approximately 300 nm for the analysis of uric acid.

11. The apparatus according to claim 1, wherein at least one of the absorption sensor or a light source for the absorption sensor operate in a wavelength range with a range of substantially +/−1 nm to 5 nm.

12. A method for the quantitative concentration determination of selected or selectable substances such as uremic toxins in a fluid, preferably for the determination of a quality measure for the dialysis such as the concentration of selected toxic substances or for the determination of a removed total quantity of uremic toxins during the dialysis with a dialysis apparatus, wherein the method comprises the steps of:
   detecting, by an optical absorption sensor, at least one first extinction signal of the fluid at at least one analysis wavelength at a first pH value of the fluid;
   adjusting, by a pH adjusting device, the fluid to a second pH value of the fluid which differs from the first pH value;
   detecting, by the absorption sensor, at least one second extinction signal of the fluid at the analysis wavelength at the second pH value;
   processing the two extinction signals at the first and the second pH values to obtain a result and determining an absolute concentration or a signal proportional to the concentration of at least one selected substance dissolved in the fluid on the basis of the result of processing; and
   adjusting, with an analysis wavelength adjusting device, the analysis wavelength to a value at which the selected or selectable substance changes its absorption property if the pH value changes.

13. The method according to claim 12, wherein the fluid is excreted from a body, extracted from the body, or is an extra corporeal blood purification fluid.

14. The method of claim 12, wherein the result is obtained by calculating a difference between the two extinction signals.

15. The method according to claim 12, wherein in the case of overlapping absorption bands of the selected substance and at least one further, non-selected substance, the at least one predetermined analysis wavelength is an isosbestic analysis wavelength with respect to the non-selected substance.

16. The method according to claim 15, wherein the at least one predetermined analysis wavelength is adjusted to approximately 254 nm for the analysis of creatinine, corresponding to the isosbestic point of uric acid and/or approximately 300 nm for the analysis of uric acid.

* * * * *